United States Patent [19]
Yasutake

[11] Patent Number: 5,742,172
[45] Date of Patent: Apr. 21, 1998

[54] SCANNING PROBE MICROSCOPE AND METHOD FOR OBTAINING TOPOGRAPHIC IMAGE, SURFACE POTENTIAL IMAGE, AND ELECTROSTATIC CAPACITANCE DISTRIBUTION IMAGE

[75] Inventor: Masatoshi Yasutake, Chiba, Japan

[73] Assignee: Seiko Instruments Inc., Japan

[21] Appl. No.: 728,942

[22] Filed: Oct. 11, 1996

Related U.S. Application Data

[63] Continuation of Ser. No. 441,975, May 12, 1995, abandoned.

[30] Foreign Application Priority Data

May 23, 1994 [JP] Japan ................... 6-108756

[51] Int. Cl.$^6$ .................................................. G01R 11/00
[52] U.S. Cl. ................................. 324/754; 324/750
[58] Field of Search ........................ 324/73.1, 158.1, 324/754, 758, 767, 662, 750; 250/306, 307, 423 F, 443.1; 73/105

[56] References Cited

U.S. PATENT DOCUMENTS

| Re. 32,457 | 7/1987 | Matey | 250/307 |
|---|---|---|---|
| 4,851,671 | 7/1989 | Pohl | 250/306 |
| 5,065,103 | 11/1991 | Slinkman et al. | 324/158.1 |
| 5,304,924 | 4/1994 | Yamano et al. | 324/758 |

Primary Examiner—Vinh P. Nguyen
Attorney, Agent, or Firm—Adams & Wilks

[57] ABSTRACT

A scanning probe microscope used for obtaining a surface topographical image, a surface potential image and an electrostatic capacitance distribution includes a probe having a tip attached to a lever, an oscillator for oscillating the probe in close proximity to a specimen, a displacement detector for detecting the probe oscillations and outputting a displacement signal in accordance therewith, a positioning device for relative positioning of the probe tip with respect to the specimen in the X and Y directions and for controlling the distance between the probe tip and the specimen in the Z direction, an AC voltage source for applying an AC voltage between the probe to oscillate the probe at a composite frequency having components at $\omega$ and $2\omega$, a DC voltage source for applying a DC voltage between the probe and the specimen to maintain the $\omega$ amplitude component of the probe oscillation at zero to enable the calculation of a surface potential of the specimen in accordance with the DC voltage and to enable the calculation of an electrostatic capacitance between the specimen and the probe in accordance with the $2\omega$ amplitude component of the probe oscillation, and a display device responsive to the phase difference between an output of the oscillator and the displacement signal for indicating when the probe collides with the surface of the specimen.

24 Claims, 5 Drawing Sheets

SCANNING PROBE MICROSCOPE AND METHOD FOR OBTAINING TOPOGRAPHIC IMAGE, SURFACE POTENTIAL IMAGE, AND ELECTROSTATIC CAPACITANCE DISTRIBUTION IMAGE

This is a continuation of application Ser. No. 08/441,975 filed May 12, 1995, now abandoned.

BACKGROUND OF THE INVENTION

The present invention generally relates to a measurement apparatus, and more specifically relates to a scanning probe microscope for scanning a surface of a specimen at a resolution on the order of a subnanometer to obtain surface configuration information, surface electric property information such as surface potential information and a surface electrostatic capacitance distribution.

Measurement of the surface potential was introduced by Y. Martin et al. using AFM which controls a Z-axis by an attractive force between a specimen and a probe (J. Applied physics 61 (10) 15 May, 1987). Further, a method of applying an AC electrostatic force to a probe attached to a lever is proposed by J. M. R. Weaver et al. (J. Voc, Sci., Technol B9 (1991) 1559). A measurement of a contact potential between different kinds of metals is introduced by M. Nonnenmacher et al. (Appl, Phys. lett. 58 (1991) 2921).

However, none of the reports mentioned above discloses methods to obtain a correct surface potential, such as control system of the Z-axis a, method for improving a resolution of an obtained image a, method for measuring an absolute potential or a method for removing a contact potential due to a material difference between a probe and a specimen composed of an electric circuit. The conventional control method could not achieve an accurate measurement because of a physical contact between a specimen surface and a probe. In order to avoid such contact, a gap between the specimen and the probe is set widely, which degrades the measurement a resolution of an uneven surface image. Further, the measurement is conducted in air, which could not measure an absolute potential of the specimen.

On the other hand, the measurement of a potential of an electric circuit specimen is affected by a contact potential due to a material difference between the probe and the specimen.

SUMMARY OF THE INVENTION

In order to solve the above noted problems, and object of the present invention is to obtain the surface potential and the electrostatic capacitance distribution of the specimen under a perfect noncontact condition at a resolution on the order of a subnanometer.

Figure 1:
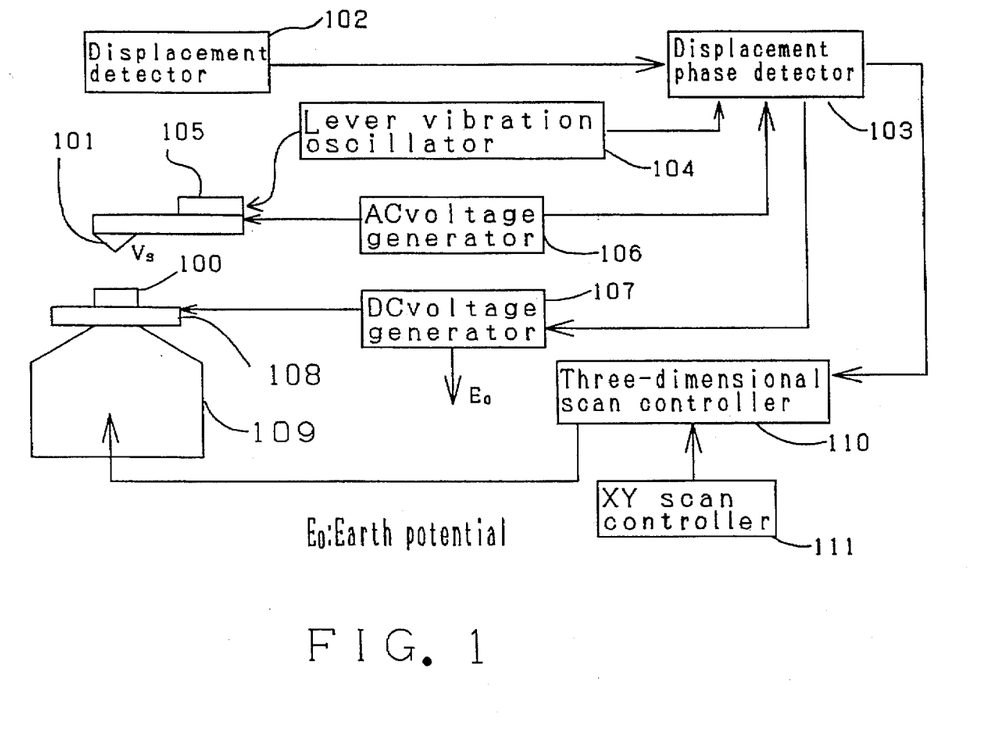
FIG. 1 is a functional diagram of a scanning probe microscope for measuring a potential difference and an electrostatic capacitance distribution.

FIG. 1 is a functional diagram of the present invention. The inventive scanning probe microscope has a probe 101 with a lever disposed in close proximity to a specimen 100. A lever vibrating oscillator 104 and a vibration source 105 are used to vibrate the electroconductive lever and probe 101. On the other hand, an AC voltage generator 106 and a DC voltage generator (voltage feedback circuit) 107 are interposed between the electroconductive lever 101 and a specimen stage electrode 108 so as to apply an AC voltage and a DC voltage. Further, a displacement detector 102 detects a vibration amplitude of the lever 101, and a displacement phase detector 103 detects a mean value of respective angular frequencies, as described below, which are provided as a Z-input signal for control of the DC voltage generator 107 and for control of a three-dimensional scan controller 110. Further, the three-dimensional scan controller 110 provides an output corresponding to X and Y signals of an XY scan controller 111, and another output corresponding to the Z-signal. These outputs are fed to a three-dimensional scanner 109 to scan a given region of the specimen to obtain three-dimensional image data while controlling a specimen/probe gap.

Hereinafter, operation of the present apparatus is described. An electrostatic coupling force caused between the lever-attached probe 101 and the specimen stage 108 is represented by a relation (1) where C denotes an electrostatic capacitance therebetween, Z denotes the gap and V denotes a voltage.

$$F_{es} = -\frac{1}{2}\left(\frac{\partial C}{\partial Z}\right)V^2 \tag{1}$$

The voltage V is represented by a relation (2) where $V_{AC}$ Sin $\omega t$ denotes a voltage from the AC voltage generator 106, $V_{off}$ denotes a voltage from the DC voltage generator 107, and $V_S$ denotes a surface potential to be measured.

$$V = (V_s + V_{off}) + V_{AC}\sin\omega t \tag{2}$$

The relation (2) is introduced into the relation (1) to obtain a relation (3).

$$F_{es} = -\frac{1}{2}\left(\frac{\partial C}{\partial Z}\right)\left[\left\{(V_s + V_{off})^2 + \frac{V_{AC}^2}{2}\right\} + \right. \tag{3}$$
$$\left. 2(V_s + V_{off})V_{AC}\sin\omega t - \frac{V_{AC}^2}{2}\cos 2\omega t\right]$$

This electrostatic force causes the lever to vibrate at $\omega$ and $2\omega$ when the lever-attached probe 101 approaches the specimen. In turn, the lever-attached probe is forcibly vibrated at a resonance frequency $\omega r$ of the lever by the lever vibrating oscillator 104 and the vibration source 105. Accordingly, when the lever approaches the vicinity of the specimen, a vibration amplitude around $\omega r$ is attenuated from a constant vibration amplitude $A_0$ by a value $\Delta A$ represented by a relation (5) under a Van der Waals force represented by a relation (4) between the specimen and the probe and the electrostatic force.

$$F_{vdw} = -\frac{H}{Z^6} \quad (H: \text{Hamaker constant}) \tag{4}$$

$$\Delta A = \frac{2A_0Q}{3\sqrt{3K}}\left(\frac{\partial F_{vdw}}{\partial Z} + \frac{\partial F_{es}}{\partial Z}\right) \tag{5}$$

(K: Elastic constant of lever, Q Q value of lever)

The displacement detector 102 detects the vibration amplitude of the lever, and the displacement phase detector 103 detects mean values of the respective angular frequencies $\omega r$, $\omega$ and $2\omega$. Hereinafter, the respective signal components are described. The $\omega r$-component is represented by a relation (6).

The three-dimensional scan controller 110 and the three-dimensional scanner 109 are operated to control the Z-direction distance between the probe and the specimen so as to $$\overline{\Delta A} = \frac{2A_0 Q}{3\sqrt{3K}} \left( \frac{\partial F_{vdw}}{\partial Z} + \frac{\partial F_{es}}{\partial Z} \right) \quad (6)$$

$$= \frac{2A_0 Q}{3\sqrt{3K}} \left[ \frac{H}{Z^7} + \frac{1}{2} \left( \frac{\partial^2 C}{\partial Z^2} \right) \left\{ (V_s + V_{off})^2 + \frac{V_{AC}^2}{2} \right\} \right]$$

keep the average value of ΔA constant, while the XY scan controller 111 is operated to carry out an image scanning to obtain a topographic image under the constant Van der Waals force and the constant electrostatic force.

A mean vibration amplitude (mean value of Aω) of the ω-component is obtained by the following relation (7).

$$\overline{A_\omega} = -\left( \frac{\partial C}{\partial Z} \right)(V_s + V_{off})V_{AC} \quad (7)$$

The DC voltage generator 107 is operated to control a potential between the probe and the specimen (namely, $V_s = -V_{off}$) so as to keep the mean value of Aω to zero. Consequently, the surface potential $V_S$ is determined regardless of a magnitude of (δC/δZ).

A mean vibration amplitude (mean value of A2ω) of the 2ω-component is determined by the following relation (8).

$$\overline{A_{2\omega}} = \left( \frac{\partial C}{\partial Z} \right) \frac{V_{AC}^2}{4} \quad (8)$$

Thus, the electrostatic capacitance distribution is obtained in terms of a value of (δC/δZ) since $V_{AC}$ is known.

DETAILED DESCRIPTION OF THE INVENTION

Figure 3:
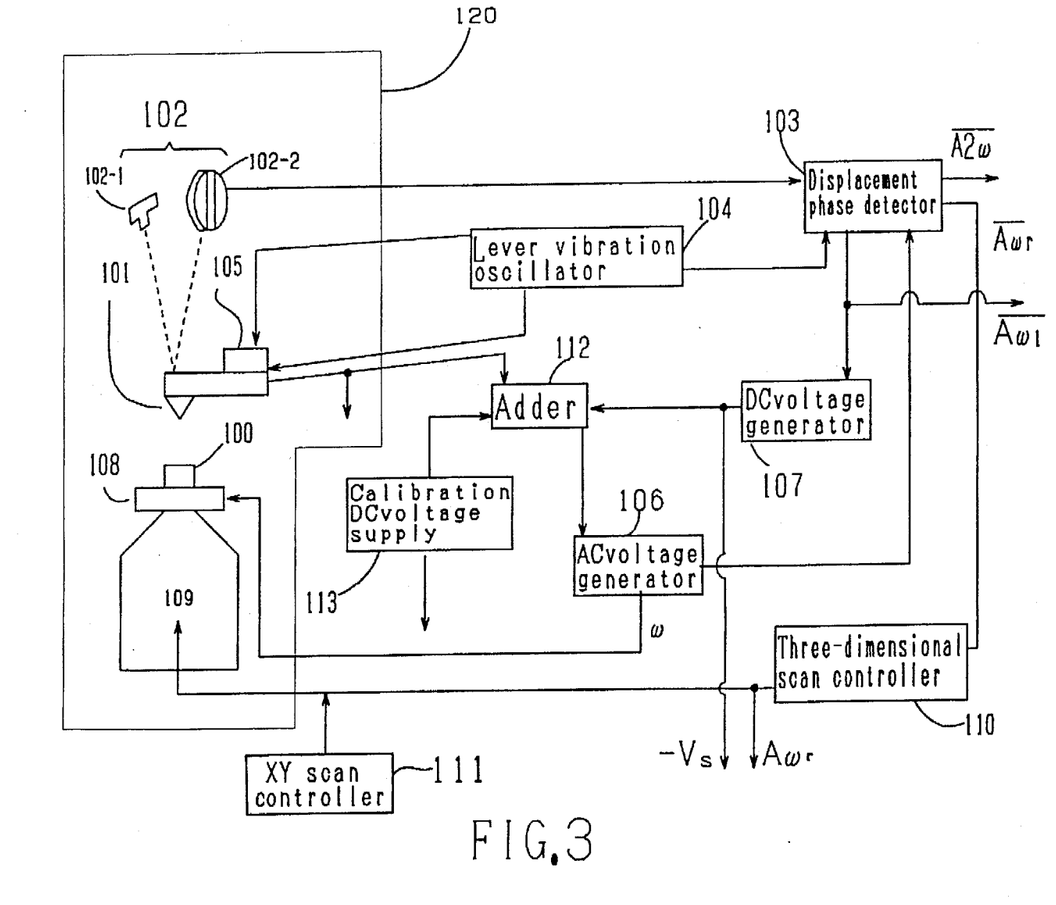
FIG. 3 is a functional diagram of a Z-axis control system in the scanning probe microscope for measuring a potential difference and an electrostatic capacitance distribution.

Hereinafter, one embodiment of the invention is described in conjunction with FIG. 3. Here, the displacement detection of the levers attached probe 101 is conducted by using an AFM of an optical lever type. First, its construction is described. In FIG. 3, 100 denotes a specimen (metal or insulative thin film having a thickness up to 100 μm), 101 denotes a lever-attached probe made of an electroconductor or coated by metal (generally, coated by gold), 102 denotes a displacement detector of the optical lever type, 103 denotes a displacement phase detector, and 104 denotes an oscillator to vibrate the lever by an output $V_r$ sin ω$_r$t where an amplitude $V_r$ ranges from 1–5V, and an angular frequency ω$_r$ is tuned to the resonance angular frequency ω$_r$ of the lever (about several tens of KHZ). Reference numeral 105 denotes a vibration source composed of a piezo plate or else having a resonance frequency sufficiently higher than the resonance angular frequency ω$_r$ of the lever. Reference numeral 106 denotes an AC voltage generator for outputting $V_{AC}$ sin ωt where an amplitude $V_{AC}$ variably ranges from 0–10V, and the angular frequency ω is variably set under the condition 2ω>>ω$_r$. 107 denotes a DC voltage generator (voltage feedback circuit) for maintaining a potential between the probe and the specimen at a predetermined voltage (generally, 0V). 108 denotes a specimen stage electrode (generally, coated with gold) which forms a capacitor together with the lever-attached probe 101. 109 denotes a three-dimensional piezo scanner for controlling a gap between the probe and the specimen together with a Z-servo system 110. 111 denotes an XY scan controller for scanning the aforementioned three-dimensional scanner in the X and Y directions. 112 denotes an adder for adding a previous output of the voltage feedback circuit 107 to an output of an external calibration voltage supply 113.

Next, description is given for positional control of the Z-direction needed for an accurate measurement of the surface potential. In order to accurately measure the surface potential and the electrostatic capacitance distribution, the probe must be held at a constant gap from the specimen to accurately trace the specimen surface. In order to satisfy this condition, the Z-axis control of the probe is conducted as follows.

Figure 2:
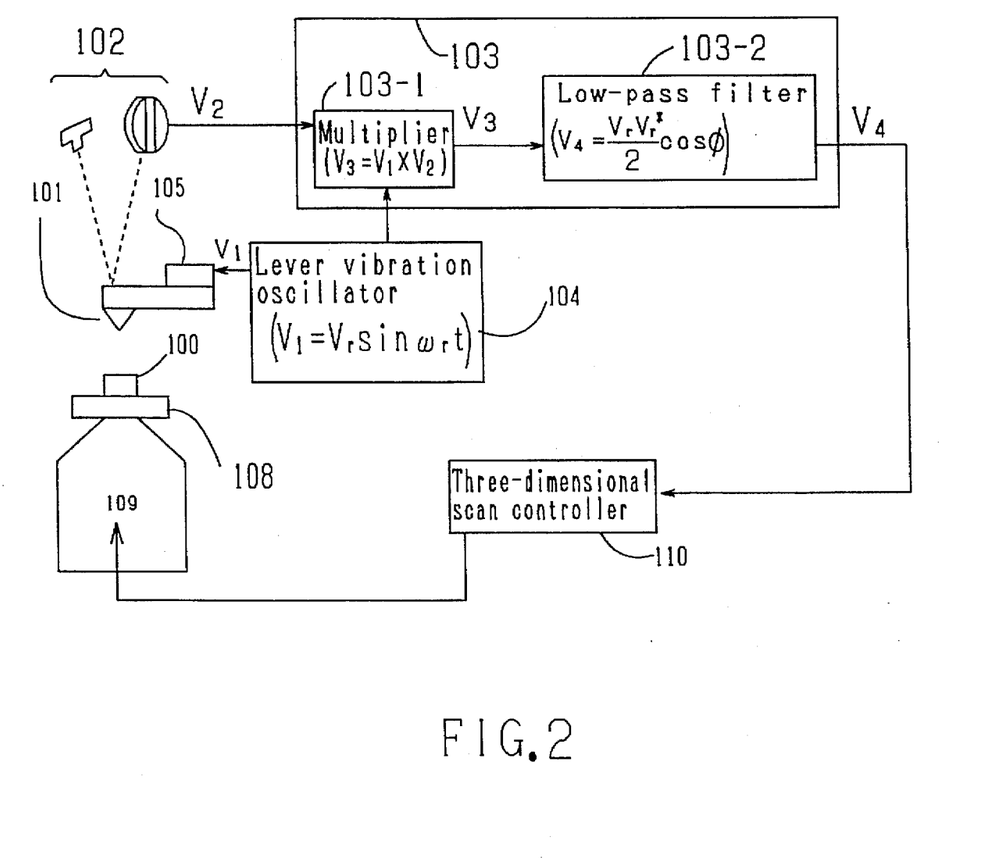
FIG. 2 is a structural diagram of the scanning probe microscope for measuring a potential difference and an electrostatic capacitive distribution.

FIG. 2 is a functional diagram of the Z-axis control system. As shown in FIG. 2, an output signal of the lever vibration oscillator 104 is represented by a relation (9).

$$V_1 = V_r \sin \omega_r t \quad (9)$$

A detection signal of the displacement detector 102 is represented by a relation (10) where $V_r^*$ denotes an amplitude and φ denotes a phase delay.

$$V_2 = V_r^* \sin(\omega_r t + \phi) \quad (10)$$

These two signals are processed by a multiplier 103-1 of the displacement phase detector (ωr channel) 103 to obtain a relation (11).

$$V_3 = V_1 V_2 = \frac{V_r V_r^*}{2} \{\cos(2\omega_r t + \phi) + \cos\phi\} (11)$$

Then, this is passed to a low-pass filter 103-2 (cutoff frequency ωC<<ω$_r$) to obtain an output $V_4$ represented by a relation (12).

$$V_4 = \frac{V_r V_r^*}{2} \cos\phi \quad (12)$$

This output $V_4$ is inputted into the Z-servo system 110 so that the three-dimensional scanner 109 controls the probe/specimen gap so as to keep the output $V_4$ constant. In case the probe periodically tends to collide with the specimen surface, the phase φ is greatly delayed at that moment so that the output $V_4$ periodically varies. Consequently, the three-dimensional scanner 109 swings in the Z-direction to indicate a periodic noise on an image signal. Namely, since a large phase delay due to the tip's contact with the specimen surface brings as the same result as that when a large attractive force is applied to the tip, the Z-servo system lifts the tip rapidly. The image at this position is consequently displayed as a luminescent spot, which shows that an accurate potential measurement has not been conducted. Such a phenomenon occurs when the vibration amplitude of the probe exceeds the probe/specimen gap, or when control parameters of the Z-servo system become too great so that the servo system oscillates.

Accordingly, the probe/specimen gap and the servo constants are set by the user to avoid generation of such a periodic noise as the luminescent spot on the topographic image, thereby enabling the probe to trace the specimen surface at a constant gap to obtain the accurate surface potential.

Next, a description is given for the different modes of measurement with reference to FIG. 3. Normally, the mean value of $A\omega r$ from the displacement phase detector 103 is supplied to the Z-servo system 110 so that the output of the Z-servo system indicates the topographic image of the specimen surface and the mean value of $A\omega_1$ indicates the surface potential. This signal is supplied to the DC voltage generator 107 so that the voltage $(-V_S=V_{off})$ effective to keep $A\omega=0$ of the relation (7) indicates the surface potential. Normally, this voltage feedback mode is adopted in the range $\pm 10V$ of the surface potential. Further, the mean value of $A2\omega$ presents a spatial distribution of a differentiated value of the electrostatic capacitance. Next, when the surface potential exceeds an allowance range (for example, $\pm 10V$) of the feedback voltage supply 107, the mean value of $A\omega_1$ is directly measured without using the voltage feedback circuit 107, while a known DC voltage is applied from the calibration DC voltage supply 113 under the condition of the same probe and the same control so as to calibrate the surface potential $V_S$ by the mean value of the measured $A\omega_1$.

This mode is called a voltage calibration mode which realizes the measurement of the surface potential up to several hundreds V. In this mode of the measurement, a high voltage is generated between the probe and the specimen, hence the distance therebetween must be set over 100 nm.

Figure 4:
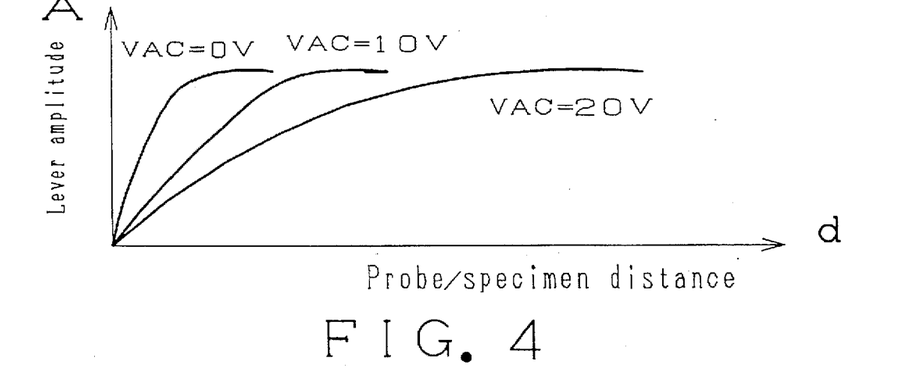
FIG. 4 is a diagram showing a relation between a lever amplitude and a probe/specimen distance while an AC applied voltage is set as a parameter.

Next, the image scanning mode is described. The microscope can concurrently measure the topographic image (surface topography image), the surface potential image, and the electrostatic capacitance distribution image as indicated by the relations (6), (7) and (8). Accordingly, three measurement channels are required for the concurrent measurement. In turn, as shown by the relation (7), the detection sensitivity of the surface potential image is improved as the applied AC voltage ($V_{AC}$) is increased. However, the resolution of the topographic image is decreased as indicated by the relation (6) and FIG. 4.

The image scanning is carried out according to the following steps in order to solve the above noted problem.

(1) The first scanning of the Z-direction is carried out under a condition where the AC voltage ($V_{AC}$) is set so as to ensure a high resolution of the surface potential (for example, $V_{AC}=20V$) to retrieve the potential difference data and the electrostatic capacitance data.

(2) Then, the same line is scanned in the −X-direction to return to a start point.

(3) Next, while the AC voltage is set to 0V($V_{AC}=0V$), the same line is scanned in the X-direction to retrieve the topographic image data under the good resolution condition.

Figure 5:
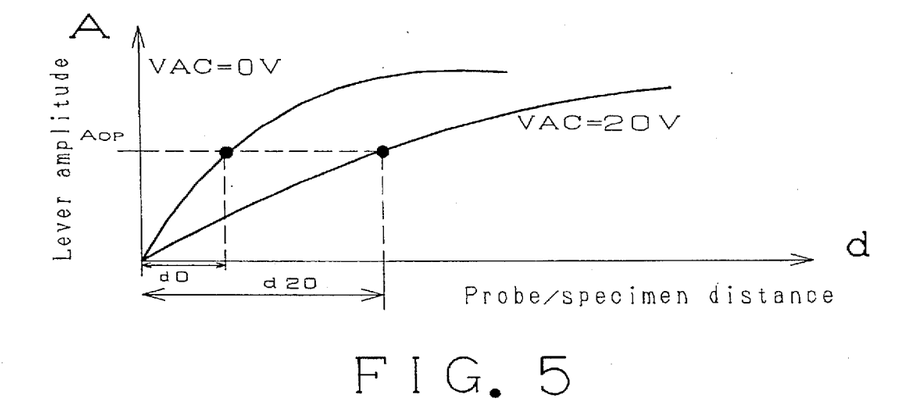
FIG. 5 is a diagram showing a relation between the lever amplitude and the probe/specimen distance (measured when scanning at the same operating point $A_{OP}$) while the AC applied voltage is set as a parameter.

(4) Further, the same line is scanned in the −X-direction to return to the start point. Next, the scanning is shifted in the Y-direction by one line to repeat the steps of (1)–(4) to retrieve one image. Accordingly, one frame scanning can produce the three of the potential difference image, the electrostatic capacitance image and the topographic image. When retrieving the topographic image data, the probe/specimen distance is set to $d_0$ as shown in FIG. 5, while the probe/specimen distance is changed to $d_{20}$ when retrieving the potential difference image and the electrostatic capacitance image. In this case, the servo setting condition $A_{OP}$ is identical, while $V_{AC}$ is controlled to change the probe/specimen distance. Such a scanning can produce the topographic image with a good resolution.

Next, the measurement method of the absolute potential is described. The present microscope would ideally determine the specimen surface potential $V_S$ with reference to $E_0$ (earth potential) shown in FIG. 1. However, it is practically difficult to obtain the absolute potential according to the following reasons. There are structural noises such as penetration of an external noise of the $\omega$-component into the displacement detector 102, and drift and offset of outputs from the displacement phase detector 103 and the DC voltage generator 107. Further, another factor is that the surface potential is varied by contamination and contact of the specimen 100 and the lever-attached probe 101.

Here, the structural noise may be rather stable and has a small time-variation. Therefore, variations around the probe and the specimen surface is reduced by the following methods.

(1) A standard specimen 100-S (a small piece of Si wafer) and the lever-attached probe for the measurement are concurrently coated by the same metal (generally, gold) by sputtering.

Figure 6:
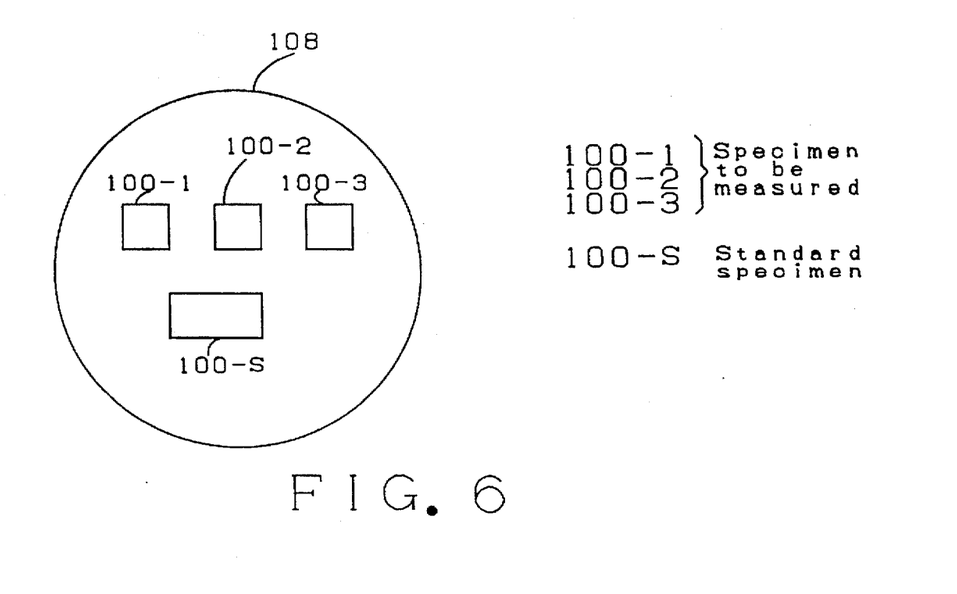
FIG. 6 shows a specimen stage.

(2) Specimens 100-1 through 100-3 to be measured and the standard specimen are set on the specimen stage electrode 108 shown in FIG. 6.

(3) The environment around the measurement unit (FIG. 3, 120) or the probe 101 and the specimen 100 is replaced by dry nitrogen gas or the like. This is to prevent the specimen and the probe from being contaminated by moisture and dust in the air.

(4) The standard specimen 100-S is measured to obtain a potential $E_{S1}$. Then, the actual specimen 100-1 is measured to obtain a potential $E_{11}$. The potential of the specimen 100-1 is determined by $E_{100-1}=E_{11}-E_{S1}$.

(5) The specimens 100-2, 100-3 are similarly measured to obtain $E_{100-2}$, $E_{100-3}$.

In the above described measurement method, even if measurement error of the surface potential of the specimen increases due to contamination of the probe, the potential of the actual specimen is measured with reference to the potential between the standard specimen and the probe. Accordingly, the correct absolute potential of the respective specimens can be obtained if the structural noise is not so added during the measurement.

Figure 7:
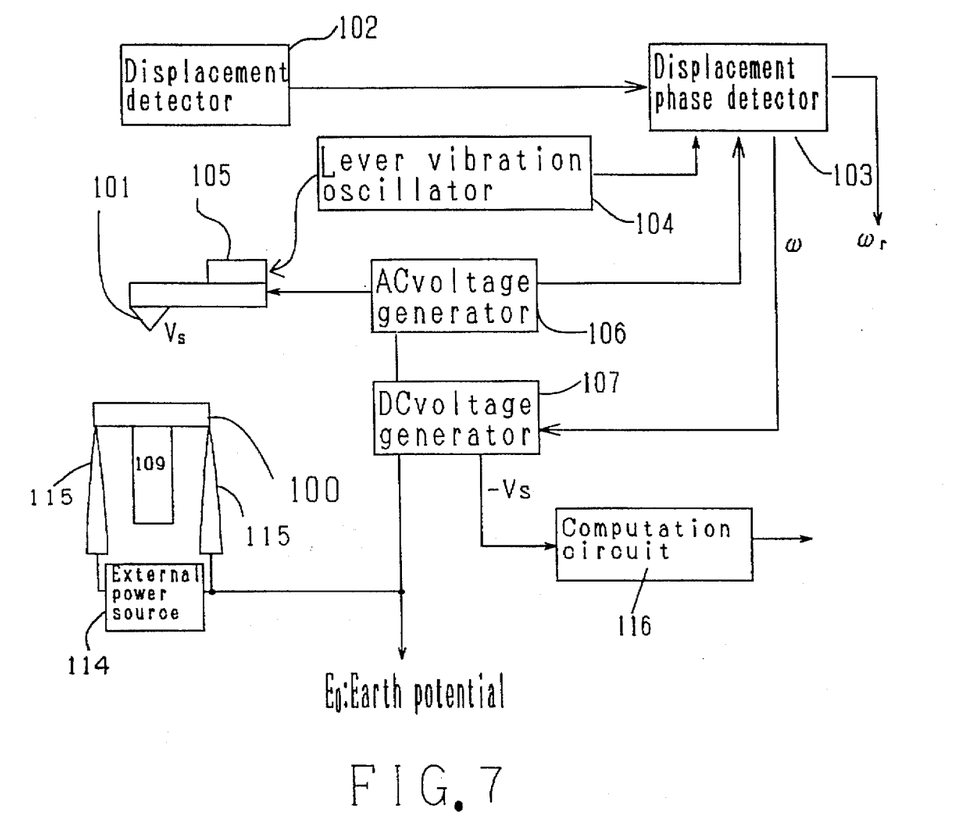
FIG. 7 shows a measurement of an electric circuit specimen.

Next, a measurement example of an electric circuit or else is shown in FIG. 7. The specimen 100 (electric circuit) is placed on the three-dimensional scanner 109. An external voltage supply 114 applies a voltage $E_{114}$ between ends of the probes 115. One of the probes 115 is set identical to the earth potential $E_0$ of the DC voltage generator 107. The potential of a desired point of the specimen 100 is measured according to the following steps.

The external voltage supply 114 is turned on and off for each of pixels or scanning lines to be measured, thereby obtaining respective surface potentials $V_{SON}$ and $V_{SOFF}$. The surface potential $V_{SOFF}$ indicates a contact potential due to a material difference between the probe and the specimen. Accordingly, a computation circuit 116 calculates $V_S=V_{SON}-V_{SOFF}$. The $V_S$ indicates a potential generated in the circuit specimen by the external voltage source 114 for each pixel or each scanning line.

According to the invention, the surface potential and the electrostatic potential distribution of the specimen are accurately obtained. Further, the probe/specimen distance is varied during the scanning to obtain the topography image with a good resolution. Further, the environment around the specimen and the probe is controlled while using a standard specimen sputter-coated by the same metal as the probe, thereby obtaining an absolute value of the specimen surface potential, which could not be measured conventionally. Further, a specific probe is provided for the measurement of an electric circuit specimen while the external voltage supply is turned on and off, thereby enabling a correct measurement of a potential response of the sample circuit by the external voltage supply while removing the contact potential due to a material difference between the probe and the circuit specimen.

What is claimed is:

1. A scanning probe microscope comprising: a probe extending in a Z direction attached to an electroconductive lever; oscillator means for producing a resonance signal to oscillate the probe at a resonance frequency $\omega_r$ thereof in close proximity to a specimen; displacement detecting means for detecting the lever vibration and producing a corresponding displacement signal according to a change in a resonant amplitude and phase around the resonance frequency $\omega_r$ of the lever; positioning means responsive to the displacement signal for scanning one of the probe and the specimen in X and Y directions and extending and retracting one of the probe and the specimen in the Z-direction so as to control the relative distance between the probe and the specimen; means for vibrating the lever at an applied angular frequency $\omega$ and at a doubled angular frequency $2\omega$ by use of electrostatic coupling between the probe and the specimen; means for applying a DC voltage between the specimen and the probe so as to maintain the average amplitude of an $\omega$-component of the probe vibration at zero to permit detection of a surface potential of the specimen in accordance with the DC voltage and to permit detection of an electrostatic capacitance of the specimen; displacement phase detecting means for detecting the respective amplitude components of said lever vibration and a phase difference between an $\omega_r$ component of said lever vibration and that of an output of said oscillator means, and for multiplying the phase difference component and the amplitude of the $\omega_r$ component, the multiplied value being input to said positioning means for controlling the Z-direction distance between the probe and the specimen in order to keep the multiplied value constant, so that the collision of the probe and a surface of the specimen can be detected since such a collision results in the positioning means separating the probe and the specimen rapidly due to a large phase delay in response to the collision.

2. A scanning probe microscope according to claim 1; wherein the positioning means includes means for scanning the probe across the surface of the specimen in the X and Y directions and adjusting the distance between the specimen and the probe in the Z-direction to set a different distance depending upon whether a measured characteristic is a surface topography or one of a surface potential and an electrostatic capacitance in order to obtain a surface configuration image, a surface potential image and an electrostatic capacitance distribution image having an optimized resolution.

3. A scanning probe microscope according to claim 1; further comprising an electric voltage supply; and means for selectively activating and deactivating the electric voltage supply in cooperation with the positioning means for applying a potential distribution across the specimen for each pixel or each line scanned by the positioning means in the X and Y directions so as to measure an electric response of the specimen and to remove a contact potential caused by a difference in materials of the probe and the specimen.

4. A scanning probe microscope comprising: a probe having a lever and a probe tip, the probe tip being disposable proximate a surface of a specimen; an oscillator for oscillating the probe at a resonant frequency $\omega_r$ of the probe; AC signal generating means for applying an AC voltage between the probe tip and the specimen to generate an alternating electrostatic force to oscillate the probe at a composite frequency having an amplitude component at a first frequency $\omega$ and an amplitude component at a second frequency $2\omega$; displacement detecting means for detecting an amplitude and a frequency of oscillation of the probe; displacement phase detecting means receptive of outputs from the displacement detecting means, the oscillator, and the AC signal generating means for detecting the respective amplitude components at frequencies $\omega_r$, $\omega$ and $2\omega$ of the probe oscillation and for determining a phase difference between the amplitude component at $\omega_r$ and an output signal of the oscillator; positioning means responsive to the phase difference for rapidly separating the probe and the sample when the probe tip comes in contact with the sample; such that a surface potential image of the specimen may be produced in accordance with the $\omega$ amplitude component of the probe oscillation, an electrostatic capacitance distribution image of the specimen may be produced in accordance with the $2\omega$ component of the probe oscillation, and a topographical surface profile image of the specimen may be produced in accordance with the $\omega_r$ component of the probe oscillation.

5. A scanning probe microscope according to claim 4; further comprising DC voltage generating means for applying a DC voltage between the specimen and the probe so as to maintain the $\omega$ amplitude component of the probe vibration at zero; and means for determining a surface potential of the specimen in accordance with an output of the DC voltage generating means.

6. A scanning probe microscope according to claim 4; further comprising calibration means including a DC voltage supply for applying a DC voltage between the specimen and the probe tip to obtain the surface potential of the specimen.

7. A scanning probe microscope according to claim 4; wherein the AC signal generating means includes means for applying a different AC signal between the probe tip and the specimen depending upon whether a measured characteristic is a surface topography, a surface potential, or an electrostatic capacitance, so as to produce a topographical image, a surface potential image, and an electrostatic capacitance distribution image at an optimized resolution.

8. A scanning probe microscope according to claim 7; further comprising means for applying a potential distribution across the specimen to test the electrical response of the specimen.

9. A scanning probe microscope according to claim 8; further comprising DC voltage generating means for applying a DC voltage between the specimen and the probe so as to maintain the $\omega$ amplitude component of the probe vibration at zero; and means for determining a surface potential of the specimen in accordance with an output of the DC voltage generating means.

10. A scanning probe microscope according to claim 9; wherein the means for applying a potential distribution comprises a voltage supply having a pair of contacts electrically connectable to the specimen, one of the contacts being further connected to a ground terminal of the DC voltage generating means.

11. A scanning probe microscope comprising: a probe having a probe tip attached to an electroconductive lever; oscillator means for oscillating the probe in close proximity to a specimen; displacement detecting means for detecting the probe oscillation and outputting a displacement signal in accordance with a change of a resonant amplitude of the probe and a phase of the probe oscillation around a resonance frequency of the lever; positioning means for relative positioning of the probe tip with respect to the specimen in X and Y directions and for controlling the distance between the probe tip and the specimen in a Z direction; means for applying an AC voltage between the probe and the specimen to generate an alternating electrostatic force to oscillate the probe at a first amplitude component having a first frequency $\omega$ and a second amplitude component having a second frequency $2\omega$; means for applying a DC voltage between the probe and the specimen so as to maintain the average value of an $\omega$ amplitude component of the probe oscillation at zero to enable the calculation of a surface potential of the specimen in accordance with the DC voltage and to enable the calculation of an electrostatic capacitance of; wherein the positioning means is responsive to a phase difference between an output of the oscillator means and the displacement signal for rapidly separating the probe and the specimen due to a large phase delay when the probe collides with a surface of the specimen to thereby enable detection that a measured value at that point is inaccurate and to enable the setting of a correct control parameter to control the distance between the probe and the sample in the Z direction in order to avoid a variation in the measured surface potential of the specimen due to the collision.

12. A scanning probe microscope according to claim 11; wherein the means for supplying an AC voltage between the probe and the specimen includes means for setting a different AC voltage depending upon whether a measured characteristic is a surface topography, a surface potential, or an electrostatic capacitance, so as to produce topographical image, a surface potential image, and an electrostatic capacitance distribution image at an optimized resolution.

13. A scanning probe microscope according to claim 11; wherein the positioning means includes means for setting the distance between the probe and the specimen in the Z-direction to a different value depending upon whether a measured characteristic is a surface topography, or one of a surface potential and an electrostatic capacitance in order to obtain a topographical image, a surface potential image, and an electrostatic capacitance image at an optimized resolution.

14. A scanning probe microscope according to claim 11; wherein an electrostatic coupling force between the probe and the specimen is defined by the following equation:

$$F_{es} = -\frac{1}{2}\left(\frac{\partial C}{\partial Z}\right)\left(\left\{(V_s + V_{off})^2 + \frac{V_{AC}^2}{2}\right\} + 2(V_s + V_{off})V_{AC}\sin\omega t - \frac{V_{AC}^2}{2}\cos 2\omega t\right)$$

wherein $F_{es}$ denotes the electrostatic coupling force, C denotes an electrostatic capacitance between the probe and the specimen, $V_s$ denotes a surface potential of the specimen to be measured, $V_{off}$ denotes a DC voltage applied by the means for applying a DC voltage between the probe and the specimen and $V_{AC}\sin\omega t$ denotes an AC voltage applied between the probe and the specimen by the means for vibrating the probe.

15. A scanning probe microscope according to claim 11; wherein the change in resonant amplitude of the probe is defined by the following equation:

$$\overline{\Delta A} = \frac{2A_0 Q}{3\sqrt{3K}}\left(\frac{\partial F_{vdw}}{\partial Z} + \frac{\partial F_{es}}{\partial Z}\right)$$

$$= \frac{2A_0 Q}{3\sqrt{3K}}\left(\frac{H}{Z^7} + \frac{1}{2}\left(\frac{\partial^2 C}{\partial Z^2}\right)\left\{(V_s + V_{off})^2 + \frac{V_{AC}^2}{2}\right\}\right)$$

wherein $\Delta A$ denotes the change in resonant amplitude caused by Van der Waals forces between the probe and the specimen, $A_0$ denotes a constant resonant amplitude of probe vibration, Q is a Q value of the lever, K denotes an elastic constant of the lever and $F_{vdw}$ denotes a Van der Waals force between the probe and the specimen.

16. A scanning probe microscope according to claim 15; wherein the positioning means includes means for controlling a Z-direction distance between the probe and the specimen so as to keep the average value of $\Delta A$ constant while scanning one of the probe and the specimen in the X and Y directions to carry out an image scanning to obtain a topographic image under constant Van der Walls forces and constant electrostatic forces.

17. A scanning probe microscope according to claim 15; wherein the means for applying a DC voltage between the specimen and the probe includes means for controlling the DC potential between the specimen and the probe such that $V_S = -V_{OFF}$ such that an amplitude component at frequency $\omega$ is maintained at zero to thereby enable calculation of the surface potential of the specimen.

18. A scanning probe microscope according to claim 11; wherein the positioning means comprises a three-directional scanner for controlling a Z-direction gap between the specimen and the probe and relatively scanning in the X and Y directions between the specimen and the probe, Z-direction servo control means for controlling the Z-direction movement of the three-directional scanner, and X and Y scan control means for controlling the X and Y movement of the three-directional scanner.

19. A scanning probe microscope according to claim 18; wherein the displacement phase detecting means includes means for multiplying an output of the oscillator means and the displacement signal and producing a multiplied output signal, filter means for filtering out a high frequency component of the multiplied output signal and producing a filtered output signal.

20. A scanning probe microscope according to claim 18; wherein the Z-direction servo control means includes means for controlling the three-directional scanner to maintain the filtered output signal constant.

21. A method for obtaining a surface topographical profile, a surface potential distribution and an electrostatic capacitance distribution of a specimen using a scanning probe microscope having a probe comprising an electroconductive lever and a probe tip, the probe tip being disposable proximate a surface of the specimen, the method comprising the steps of: applying a resonance signal having a frequency $\omega_r$ to oscillate the probe at a resonance frequency thereof in close proximity to a surface of a specimen; applying an AC voltage between the probe and the specimen to generate an alternating electrostatic force to oscillate the probe at a composite frequency having an amplitude component at a first frequency $\omega$ and an amplitude component at a second frequency $2\omega$; detecting the respective amplitude components at frequencies $\omega_r$, $\omega$ and $2\omega$ of the probe oscillation; determining a phase difference between the frequency component at $\omega_r$ and the resonance signal; detecting inaccurate data when the probe comes into contact with the specimen in accordance with the phase difference between the amplitude component at $\omega_r$ and the resonance signal; producing a surface potential distribution of the specimen in accordance with the $\omega$ component of the probe oscillation by scanning the probe with respect to the specimen while measuring the surface potential of the specimen; producing an electrostatic capacitance distribution of the specimen in accordance with the $2\omega$ component of the probe oscillation by scanning the probe with respect to the specimen while measuring the electrostatic capacitance of the specimen; and producing a topographical surface profile of the specimen in accordance with the $\omega_r$ component of the probe oscillation by scanning the probe with respect to the specimen.

22. A method according to claim 21; further comprising the steps of preventing the specimen and the probe from being contaminated by moisture and dust, measuring a surface potential of a standard specimen coated with the same conductive material as the probe, measuring the surface potential of the specimen, and subtracting therefrom the potential of the standard specimen to determine an absolute surface potential of the specimen.

23. A method according to claim 21; further comprising the steps of measuring a first surface potential of the specimen while applying a voltage potential across the specimen, measuring a second surface potential of the specimen without a voltage potential applied thereacross, and subtracting the second surface potential from the first surface potential to thereby determine the electrical response of the specimen.

24. A method according to claim 21; further comprising the step of varying a distance between the probe and the specimen depending upon whether a measured characteristic is a surface topography, or one of a surface potential and an electrostatic capacitance, in order to obtain a topographical image, a surface potential image, and an electrostatic capacitance distribution image at optimized resolutions.

* * * * *